United States Patent [19]

Cole

[11] 4,226,856
[45] Oct. 7, 1980

[54] PREPARATION AND USE OF BOUVARDIN AND DEOXYBOUVARDIN

[75] Inventor: Jack R. Cole, Tucson, Ariz.

[73] Assignee: University Patents, Inc., Norwalk, Conn.

[21] Appl. No.: 962,161

[22] Filed: Nov. 20, 1978

[51] Int. Cl.³ .................. A61K 37/00; C07C 103/52; C07G 7/00
[52] U.S. Cl. ............................. 424/177; 260/112.5 R
[58] Field of Search ................ 260/112.5 R; 424/177

[56] References Cited

PUBLICATIONS

Jolad, S., et al., J. American Chem. Soc., 99, pp. 8040–8044 (1977).

*Primary Examiner*—Delbert R. Phillips
*Assistant Examiner*—Blondel Hazel

[57] ABSTRACT

Bouvardin ($C_{40}H_{48}N_6O_{10}$) and deoxybouvardin ($C_{40}H_{48}$-$N_6O_9$), bicyclic hexapeptides isolated from *Bouvardia ternifolia* are provided in the form of pure materials, individually, and as a mixture with each other. The pure materials exhibit significant anti-neoplastic disease activity in vivo and in vitro.

9 Claims, No Drawings

PREPARATION AND USE OF BOUVARDIN AND DEOXYBOUVARDIN

The present invention relates generally to novel compositions possessing anti-neoplastic disease activity and to methods for preparing and using the same. More particularly, the invention provides two structurally related hexapeptide plant tissue isolates, as well as procedures for obtaining the isolates individually, and as mixtures with each other in pure form. Also provided are novel therapeutic methods for the treatment of neoplastic diseases in animals and novel pharmaceutical compositions suitable for use in such treatment methods.

Incorporated by reference herein is the disclosure of the activities of applicant and his co-workers appearing in the Journal of the American Chemical Society, 99, pp. 8040–8044 (1977).

BRIEF SUMMARY

Provided by the invention are the structurally related hexapeptides, bouvardin and deoxybouvardin, having the respective formulae Ia and Ib set out below.

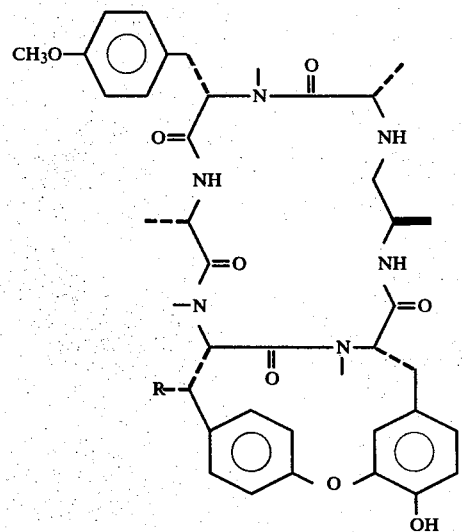

Ia, R=OH
Ib, R=H

Pure bouvardin and deoxybouvardin are isolated from *Bouvardia ternifolia* tissue according to a method comprising forming a crude, isopropyl ether-insoluble precipitate of the plant tissue following serial solvent extraction with methanol, acetonitrile, and dichloromethane. Bouvardin and deoxybouvardin are isolated from the crude precipitate and are separated from each other by chromatographic techniques.

The therapeutic methods of the invention comprise administration of from about 0.01 to about 10.0 mg/kg of the compounds to animals, subject to a neoplastic diseases including, e.g., lymphocytic leukemia, melanotic melanoma and adenocarcinoma. Pharmaceutical compositions according to the invention incorporate therapeutically effective amounts of bouvardin or deoxybouvardin in combination with a pharmaceutically acceptable carrier.

Further aspects of the present invention will become apparent upon consideration of the following detailed description.

DETAILED DESCRIPTION

The following example relates to the isolation of bouvardin and deoxybouvardin from tissue of *Bouvardia ternifolia*, a plant known in the Southwest U.S. and in Mexico by the common names "trompetilla", "tlacoxochitl", and "mirto".

EXAMPLE 1

The dry stems, leaves and flowers of *Bouvardia ternifolia* are ground in a Wiley mill and stored at −10° C. prior to extraction. In a typical procedure, 12 kg of the ground material is twice extracted for 24 hours with 60 liter aliquots of methanol with the use of a mechanical stirrer. The combined, filtered methanol extracts are concentrated in air to about 2 liters, diluted with an equal volume of a water-methanol mixture (95:5 v/v) and filtered. The filtrate is evaporated to dryness in air and thoroughly extracted three times with 2 liter aliquots of acetonitrile. The acetonitrile extract is evaporated in air to a semi-solid state, dissolved in methanol and taken to dryness under vacuum. The resulting residue (generally about 90 g) is extracted four times for two hours with stirring in 1.5 liter aliquots of dichloromethane, filtered, and evaporated in vacuo. The residue (about 19.1 g) is dissolved in a minimum of methanol and isopropyl ether is added until precipitation ceases. This mixture is allowed to stand overnight in the refrigerator (3° C.) and then filtered by decantation. The precipitate is stirred for one half hour with isopropyl ether, filtered, washed with a small amount of isopropyl ether, and vacuum dried. This provides about 6.3 g of dry, green-brown precipitate.

The crude precipitate is subjected to chromatographic separation to provide isolates of pure bouvardin and pure deoxybouvardin. According to one procedure, the 6.3 g of green-brown precipitate is first chromatographed over a column (180 g) of silica gel 60 (PF254 E. Merck). The column is eluted with hexane-dichloromethane-methanol (25:22:3, v/v/v) and fractions are combined which are similar by thin layer chromatography. The KB-active (see, infra) fraction (1.0 g) is then subjected to two consecutive preparative thick layer chromatographies, developing with hexanedichloromethane-methanol (20:27:3, v/v/v; 3 developments) and then with dichloromethane-methanol (94:6, v/v; 2 developments) for a second preparative chromatographic separation. The KB-active fraction from the first preparative separation is used for the second one. These preparative thick layer chromatographies, after decolorization, result in a colorless, amorphous mixture containing largely bouvardin (formula I, above) and deoxybouvardin (formula Ib). Separation of the two materials is achieved by preparative thin layer chromatography, the developing solvent being ether-ethyl acetate-methanol (15:35:2, v/v/v; 2 developments).

The lower $R_f$ material is deoxybouvardin (52.5 mg), obtained as a colorless powder, mp 257°–40° C., $[\alpha]_D^{25} -138°$ (c 0.7 CHCl$_3$), ms 756 (parent). Bouvardin (121.3 mg) is successfully crystallized from methanol-dicholormethane to give colorless needles, mp 254°–5° C., $[\alpha]_D^{25} -181°$ (c 1.0, CHCl$_3$), ms 772 (parent. A bouvardin impurity (showing a methyl doublet in the $^1$H nmr spectrum) is removed by recrystallization from methanol.

An alternative procedure, suitable for large scale isolations of bouvardin alone, may involve successive column chromatographies, as follows. A first silica gel 60 (30:1) treatment column is eluted with hexane-dichloromethane-methanol (20:27:3). The concentrated fraction of bouvardin and deoxybouvardin and other impurities is then chromatographed on another silica gel 50 (50:1) column eluted with ether-ethylacetate-methanol (15:35:2). The fractions containing bouvardin are decolorized with activated charcoal and chromatographed on $Al_2O_3$ (50:1) to remove methylbouvardin. The eluent is hexane-dichloromethane-methanol (20:28.5:1.5). The fractions containing bouvardin are combined and evaporated under vacuum. Bouvardin is crystallized from methanol, removed by filtration and dried under vacuum over calcium chloride for forty-eight hours.

The isolative methods of the present invention are thus seen to include the step of preparing a crude, isopropyl ether-insoluble precipitate of bouvardin and deoxybouvardin following solvent extraction of plant tissue. This step is followed by chromatographic separation of a mixture of the two substances from proteinaceous and nonproteinaceous impurities in the precipitate. Finally, bouvardin and deoxybouvardin are chromatographically separated from each other to provide pure isolates. The term "pure" as herein applied to bouvardin and deoxybouvardin shall designate that the compounds or mixture thereof with each other are more than 90 percent free of all materials naturally associated therewith within plant tissue of *Bouvardia ternifolia*.

The anti-neoplastic utility of bouvardin, deoxybouvardin, and mixtures thereof is demonstrated by the results obtained in standardized "PS", "Bl" and "KB" test systems propounded by the Drug Evaluation Branch, Drug Research and Development, Chemotherapy, National Cancer Institutes as performed by four independent screening labs—Hazelton Laboratories (TRW, Inc.) Vienna, Va; Batelle Memorial Institute, Columbus, Ohio; Southern Research Institute, Birmingham, Ala; and, IIT Research Institute, Chicago, Ill.

The in vivo "PS" tests were carried out on mice according to "Lymphocytic Leukemia P388—Protocol 1.200", published in *Cancer Chemotherapy Reports*, Part 3, Vol. 3, No. 2, page 9, (September 1972) with results reported in terms of percent survivals of test versus control animals (%T/C). According to the protocol evaluation procedures, a T/C value $\leq 85\%$ indicates a toxic test, while a T/C value $\leq 125\%$ demonstrates antitumor activity.

The in vivo "Bl" were carried out on mice according to "Melanotic Melanoma B 16—Protocol 1.300" (id., p. 11) with reporting and evaluation procedures identical to those of the "PS" test.

The in vitro "KB" tests were carried out according to "Cell Culture Screen KB—Protocol 1.600" (id., p. 17) using cells of human adenocarcinoma of the nasopharynx. Test results are expressed as the dose that inhibits cell growth to 50% of control growth by 3 days after drug addition. According to protocol evaluation criteria for pure compounds, anti-tumor activity is demonstrated by an ED $50 \leq 4$ μg/ml.

In the "PS" test, bouvardin isolated according to Example 1 exhibited activities of from 135 to 217% T/C at dose levels ranging from 0.02 to 2.0 mg/kg. Table I, below, summarizes the ranges of % T/C values obtained in approximately two hundred "PS" tests. A single value for a given dosage represents either a single test at that level or multiple tests with identical results.

TABLE I

| DOSE | RANGE OF % T/C |
| --- | --- |
| 2.00 | 167 to 205 |
| 1.00 | 148 to 217 |
| 0.50 | 135 to 186 |
| 0.25 | 161 to 188 |
| 0.16 | 158 |
| 0.11 | 150 to 164 |
| 0.07 | 139 |
| 0.04 | 134 |

In approximately seventy replications of the "I" test, bouvardin exhibited activites in the range of 134–152% T/C at doses varying from 0.12 to 2.0 mg/kg. In approximately ten replications of the "KB" test, bouvardin exhibited an average ED 50 of about $4.3 \times 10^{-7}$ μg/L.

Multiple testings of deoxybouvardin showed "PS" test activities of 142–216% T/C at 0.04 to 2.0 mg/kg doses and "Bl" test activities of 133–175% T/C at 0.25 to 8.0 mg/kg doses. The Ed 50 of deoxybouvardin in the "KB" test system averaged $1.9 \times 10^{-8}$ μg/L.

Mixtures of pure deoxybouvardin and pure bouvardin obtained according to Example 1 and not subjected to chromatographic separation from each other were also tested in the "PS", "Bl", and "KB" protocols. "PS" activity for these "natural" mixtures was 132–257% T/C at dosages of 0.12 to 2.9 mg/kg. "Bl" activity was 132–167% T/C at dosages of 0.12 to 2.0 mg/kg. "KB" test activity for the mixtures averaged less than $10^{-2}$ μg/L.

According to the therapeutic methods of the invention, bouvardin or deoxybouvardin (or mixtures thereof) is administered to animals, subject to a neoplastic disease state (e.g., lymphocytic leukemia, melanotic melanoma, and adenocarcinoma) in a dosage form of from about 0.1 to about 10.0 mg/kg.

Because pure bouvardin, pure deoxybouvardin and mixtures thereof are partially soluble in water, a wide variety of pharmaceutically acceptable aqueous- and non-aqueous-based diluents, adjuvants and carriers may be employed in preparing the pharmaceutical compositions of the invention wherein the compounds or mixtures provide the active ingredient. As one example, the "PS" and "Bl" tests noted above involved subcutaneous administration of the test compounds in simple water solution forms. It is expected that water solutions of bouvardin and deoxybouvardin would ordinarily be stabilized by addition of antioxidant substances.

Compositions of the invention may be employed according to the above-noted methods by means of a variety of administrative routes, including oral and parenteral administration. Preservation of the structural integrity of the compounds when administered orally may require use of enteric coatings and the like.

Numerous modifications and variations of the invention are expected to occur to those skilled in the art upon consideration of the foregoing description. Only such limitations as appear in the appended claims should be placed upon the invention.

What is claimed is:

1. Purified bouvardin having a purity such that it is more than 90 percent free of all materials naturally associated therewith within *Bouvardia ternifolia* tissue.

2. Purified deoxybouvardin having a purity such that it is more than 90 percent free of all materials naturally associated therewith within *Bouvardia ternifolia* tissue.

3. A purified mixture of bouvardin and deoxybouvardin, the purity of said mixture being such that it is more than 90 percent free of all materials naturally associated therewith within *Bouvardia ternifolia* tissue.

4. A method for isolation of purified bouvardin and purified deoxybouvardin from *Bouvardia ternifolia* tissue, said method comprising:
   (a) forming a crude, isopropyl ether-insoluble precipitate of bouvardin and deoxybouvardin by serial solvent extraction of *Bouvardia ternifolia* tissue with methanol, acetonitrile, dichloromethane, followed by precipitation of the final extract with isopropyl ether;
   (b) chromatographically separating and isolating a purified mixture of bouvardin and deoxybouvardin from said precipitate, the purity of said mixture being such that it is more than 90 percent free of all materials naturally associated therewith within said *Bouvardia ternifolia* tissue.

5. The method of claim 4 further including the step of chromatographically separating the purified bouvardin and the purified deoxybouvardin from each other in said mixture.

6. A method for treatment of a rodent subject to a neoplastic disease, said method comprising administering to said animal from about 0.01 to about 10.0 mg/kg of a compound selected from the group consisting of purified bouvardin, purified deoxybouvardin, or purified mixtures thereof with each other, the purity of said compound or mixture being such that it is more than 90 percent free of all materials naturally associated therewith within *Bouvardia ternifolia* tissue.

7. The method of claim 6, wherein said disease is lymphocytic leukemia.

8. The method of claim 6, wherein said disease is melanotic melanoma.

9. A pharmaceutical composition for use in treatment of a rodent subject to a neoplastic disease, said composition consisting of a therapeutically effective amount of a compound selected from the group consisting of purified bouvardin, purified deoxybouvardin, or purified mixtures thereof with each other, as an active ingredient, in combination with a pharmaceutically effective diluent, adjuvant or carrier, the purity of said compound or mixture being such that it is more than 90 percent free of all materials naturally associated therewith within *Bouvardia ternifolia* tissue.

* * * * *

UNITED STATES PATENT AND TRADEMARK OFFICE
CERTIFICATE OF CORRECTION

PATENT NO. : 4,226,856
DATED : October 7, 1980
INVENTOR(S) : Jack R. Cole

It is certified that error appears in the above—identified patent and that said Letters Patent is hereby corrected as shown below:

Column 1, Line 63, "diseases" should read -- disease --.

Column 2, Line 55, after "I" and before the comma, insert -- a --;

Line 64, "dicholormethane" should read -- dichloromethane --;

Line 65, after the word "parent" and before the period, insert the closing parenthesis.

Column 3, Line 52, before the word "were", insert -- tests --.

Column 4, Line 15, the "l" appearing between the quotation markes should read -- B1 --.

Signed and Sealed this

Third Day of February 1981

[SEAL]

Attest:

RENE D. TEGTMEYER

Attesting Officer

Acting Commissioner of Patents and Trademarks

UNITED STATES PATENT AND TRADEMARK OFFICE
CERTIFICATE OF CORRECTION

PATENT NO. : 4,226,856
DATED : October 7, 1980
INVENTOR(S) : JACK R. COLE

It is certified that error appears in the above-identified patent and that said Letters Patent are hereby corrected as shown below:

In Col. 1, prior to the first line of text, insert the following:

--The invention described herein was made in the course of work under a grant or award from the Department of Health, Education and Welfare.--

Signed and Sealed this

Third Day of November 1981

[SEAL]

Attest:

GERALD J. MOSSINGHOFF

Attesting Officer     Commissioner of Patents and Trademarks